US006375961B1

(12) United States Patent
Carson et al.

(10) Patent No.: US 6,375,961 B1
(45) Date of Patent: Apr. 23, 2002

(54) COSMETIC SKIN CARE COMPOSITIONS CONTAINING CUMIC ALCOHOL

(75) Inventors: Robert Carson, Rahway; Krupa Patel, Edison; Sreekumar Pillai, Wayne; Stewart Paton Granger, Paramus, all of NJ (US); Beth Anne Lange, Appleton, WI (US)

(73) Assignee: Unilever Home & Personal Care (USA), division of Conopoco, Inc., Greenwich, CT (US)

( * ) Notice: Subject to any disclaimer, the term of this patent is extended or adjusted under 35 U.S.C. 154(b) by 0 days.

(21) Appl. No.: 09/597,053

(22) Filed: Jun. 20, 2000

Related U.S. Application Data

(60) Provisional application No. 60/141,636, filed on Jun. 30, 1999.

(51) Int. Cl.$^7$ ................................................. A61K 7/00
(52) U.S. Cl. .......................... 424/401; 514/25; 514/474
(58) Field of Search ......................... 424/401; 514/474, 514/25

(56) References Cited

U.S. PATENT DOCUMENTS

| | | | |
|---|---|---|---|
| 5,080,901 A | 1/1992 | Hangay et al. | 424/195.1 |
| 5,565,199 A | 10/1996 | Page et al. | 424/195 |
| 5,716,800 A | 2/1998 | Meybeck et al. | 435/52 |
| 5,861,145 A | 1/1999 | Lucas et al. | 424/65 |
| 5,871,718 A | 2/1999 | Lucas et al. | 424/65 |
| 5,874,070 A | 2/1999 | Trinh et al. | 424/65 |

FOREIGN PATENT DOCUMENTS

WO   9842188   * 10/1998

OTHER PUBLICATIONS

Derwent Abstract, JP 10182416, published Jul. 7, 1998.
Derwent Abstract. JP 2204495, published Aug. 14, 1990.
Derwent Abstract, JP 6256150, published Sep. 13, 1994.
Derwent Abstract, JP 4356423, published Dec. 10, 1992.
Derwent Abstract, JP 4356424, published Dec. 10, 1992.
Derwent Abstract, JP 62181202, published Aug. 8, 1987.
Derwent Abstract, JP 9202712, published Aug. 5, 1997.
Derwent Abstract, JP 9002939, published Jan. 7, 1997.
Derwent Abstract, CN1136431, published Nov. 27, 1996.
Derwent Abstract, WO 95/22957, published Aug. 31, 1995.
Opdyke, D.L.J., Fragrance Raw Materials Monographs, Food and Cosmetics Toxicology, vol. 12, (1974), p. 871.
Poucher, W.A., Poucher's Perfumes, Cosmetics and Soaps, The Raw Materials of Perfumery, vol. 1, 1991, p. 107.

* cited by examiner

*Primary Examiner*—Michael A. Williamson
(74) *Attorney, Agent, or Firm*—Ellen Plotkin

(57) ABSTRACT

Cosmetic skin care compositions containing cumic alcohol. The inventive compositions improve transglutaminase-1 and ceramide expression in skin cells, and enhance the cell uptake of glucose and ascorbic acid.

10 Claims, No Drawings

COSMETIC SKIN CARE COMPOSITIONS CONTAINING CUMIC ALCOHOL

This application claims the benefit of U.S. provisional application No. 60/141,636 filed Jun. 30, 1999.

FIELD OF THE INVENTION

Cosmetic compositions containing cumic alcohol, and methods of improving the cosmetic appearance of the skin by applying such compositions to the skin.

BACKGROUND OF THE INVENTION

The human skin consists of two major layers, the bottom thicker layer, dermis and the top thinner layer, the epidermis. Dermis is the layer which provides the strength, elasticity and the thickness to the skin. With aging, the thickness of the dermal layer is reduced and this is believed to be partially responsible for the formation of wrinkles in aging skin. The top layer of human skin or the epidermis which provides the resilience and the barrier properties of the skin, is composed of many different cell types. Keratinocytes are the moor cell type of the epidermis (75–80% of the total number of cells in the human epidermis). Within the epidermis the, keratinocytes reside in four distinct stages of differentiation. Epidermal differentiation is important for providing the essential function of the skin, namely to provide a protective barrier against the outside environment and to prevent loss of water from the body. Formation of the cornified envelope is the final stage of keratinocyte differentiation. The enzyme responsible for the formation of cornified envelopes, transglutaminase, is a marker of epidermal differentiation.

Other factors, in addition to skin thickness, impart the barrier function to the skin. Layers of lipids in the skin form a "water barrier" which prevents water loss from the skin, and, consequently, the appearance of aged, dry or wrinkled skin. These lipids consist predominantly of ceramides, cholesterol, and fatty acids. In normal skin, if the barrier function is perturbed, the epidermis re-synthesizes the deficient lipids. Under certain conditions, however, a reduced capacity for re-synthesis may occur. This is especially so with aging or dry skin, where skin lipid levels are in any case sub-normal. In addition, cell metabolism in aging/dry skin is impaired. Decreased uptake and utilization of glucose can lead to decreased metabolism and skin cell turnover leading to the appearance of aged, dry and flaky skin.

Exposure to ultraviolet light and other environmental insuls produce free radical damage in skin cells. Antioxidants, such as ascorbates, help to reduce this damage by decreasing free radical concentrations. Any materials which stimulate the transport of antioxidants into cells may be expected to increase protection from free radical damage.

The present invention is based at least in part on the discoveries that the exposure of cultured keratinocytes to cumic alcohol results in several desirable effects: the enhancement of differentiation, the expression of lipids essential to barrier function, and increase in glucose and ascorbate uptake.

Cumic alcohol (also known as p-isopropylbenzyl alcohol) is an essential oil which is found in trace amounts in licorice root (4 ppm. U.S. Agricultural Research Service, Phytochemical and Ethnobotanical Databases). The Merck Index also lists caraway seed as a source of cumic alcohol, however, the Agricultural Research Service database does not mention cumic alcohol at all in its listing of ion-trivial chemicals in caraway. Licorice and licorice extract have been descised for use in skin care compositions. U.S. Pat. No. 5.716.800 (MeybecK et al.) mentions licorice extract as a sebum regulator. U.S. Pat. No. 5.565,199 (Page et al.) mentions the use of licorice extract material as an externally applied substance with estrogenic activity. U.S. Pat. No. 5,080,901 (Hangay et al.) mentions the use of licorice in a cosmetic and paramedical anti-inflammatory product. Other publications mention the use of licorice or licorice extract materials for various skin benefits such as sunscreen (J010182416), anti-oxidant (J02204495), whitening agent (J06256150), reduction of contact dermatitis (J04356423, J04356424), antimicrobial cosmetic preservative (J62181202, J09202712), bathing composition for dry skin (J09002939), acne cream (CN1136431) and hair growth (WO9522957).

None of the art cited above mentions cumic alcohol as an active. The Hangay patent indicates that a 50% alcohol extract of licorice root (Glycyrrhiza glabra, radix) has a dry substance content of 3.5 to 4.5%. Although an extraction process removes material from the subject of the extraction it does not raise the overall concentration of the material extracted; on the contrary it reduces it, Since the typical concentration of cumic alcohol in licorice root is 4 ppm, that concentration is reduced in the extract solvent and then further reduced in any process of formulation where the extract is used to trace levels.

U.S. Pat. No. 5,871,718 (Lucas et al.) and U.S. Pat. No. 5,874,070 (Trinh et al.) disclose odor-absorbing compositions which may be used on skin. The compositions contain cyclodextrin, which is a molecule capable of complexing odor molecules. The compositions also include a perfume, which may be cumic alcohol. Both patents teach that perfumes in the composition have a tendency go complex with cyclodextrins.

SUMMARY OF THE INVENTION

The present invention includes a cosmetic skin care composition comprising:

(a) from 0.001 to 50 wt. % of solubilized cumic alcohol of Formula 1:

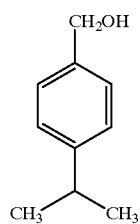

(b) a cosmetically acceptable vehicle.

Inventive compositions provide enhanced keratinocyte differentiation and enhanced lipid production and improved glucose and ascorbate uptake, which should result in improved barrier function and, consequently, reduced appearance of lines, wrinkles and aged skin, improved skin color, cosmetic treatment of dry or photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts or ratios of material or conditions of reaction, physical properties of materials and/ or use are to be understood as modified by the word "about." All amounts are by weight of the final composition, unless otherwise specified.

The term "skin" as used herein includes the skin on the face neck, chest, back, arms, legs, hands and scalp.

The term "solubilized" as used herein means that at least 90% of cumic alcohol present in the final composition is solubilized.

Cumic alcohol has the following structural formula:

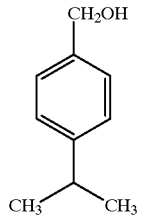

Cumic alcohol can be obtained from Sigma.

Cumic alcohol is incorporated in the inventive compositions in an amount of from 0.001 to 50%, preferably in order to maximize benefits at a minimum cost, in an amount of from 0.001 to 10%, most preferably from 0.001 to 5%.

Cosmetically Acceptable Vehicle

The composition according to the invention also comprises a cosmetically acceptable vehicle to act as a dilutant, dispersant or carrier for cumic alcohol in the composition, so as to facilitate its distribution when the composition is applied to the skin. Cumic alcohol must be solubilized and uncomplexed in order to deliver the benefits to skin. Penetration of the stratum corneum would be essential for activity. Cumic alcohol may be dissolved in alcohol for a toner composition. Preferably, the inventive compositions are oil-in-water emulsions, wherein cumic alcohol is dissolved in an oil phase. The emulsions preferably contain at least 80 wt. % water, by weight of the vehicle+Preferably, the amount of water is at least 50 wt. % of the inventive composition, most preferably from 60 to 80 wt. %, by weight of the composition.

Optional Skin Benefit Materials and Cosmetic Adjuncts

According to the present invention, among the beneficial effects of cumic alcohol is its ability to enhance glucose and ascorbic acid uptake into skin cells. While cumic alcohol enhances the uptake of endogenous glucose and ascorbic acid, the uptake may be further increased by adding an additional ingredient to the composition which is selected from the group consisting of glucose, ascorbic acid, or a compound which is known to break down in the skin to glucose or ascorbic acid.

Compounds which break down in the skin to provide glucose include, but are not limited to glucosamine, glucose glutamate, galactose, lactose, sucrose and glucose phosphate esters.

Compounds which break down in the skin to provide ascorbic acid include, but are not limited to ascorbyl palmitate, ascorbyl stearate, ascorbyl tetraisopalmitate, magnesium ascorbyl phosphate, sodium ascorbyl monophosphate, ascorbic acid polypeptide.

This preferred optional ingredient is included in the inventive compositions in an amount of from 0.001 to 10%, preferably from 0.01 to 10%, most preferably from 0.1 to 5%.

Especially preferred composition according to the invention contain glucose and/or ascobic acid, because these are available for uptake, withuot additinal metabolism in skin.

The inventive compositions preferably include suscreens to lower skin's exposure to harmful UV rays.

Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenazone) can be used. Octyl methoxycinnamate and 2-hydroxy-4-methoxy benzophenone are commercially availabe under the trademarks, Parsol MCX and Benzophenone-3, respectively. The exact amount of sunscreen employed in the emulsions can vary depending upon the degree of protection desired form the sun's UV radiation.

An oil or oily material may be presente, together with an emollient to provide either a water-in-oil emulsion or an oil-in-water emulsion, depending largely on the average hydrophilc-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, dilsopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageeran, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite lays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following specific examples further illustrate the invention, but the invention is not limited thereto.

Keratinocyte Culture

Normal human keratinocytes, isolated from neonatal foreskin by trypsin treatment, were grown in Dulbecco's Modified Eagles Medium (DMEM, Life Technologies. Grand Island, New York) with 10% fetal bovine serum in the 10 presence of irradiated mouse fibroblasts for establishing dividing keratinocyte colonies. Cells were incubated until their second passage and stored at −70 ° C. for future use. All incubations took place at 37 ° C. with 5% $CO_2$. Frozen second passage keratinocytes were thawed and plated in T-175 flasks (Corning. Corning, N.Y.) with DMEM and grown for five days. After reaching 80% confluence, they were trypsinized and seeded into 6-well plates containing keratinocyte growth medium (KGM, Clonetics, San Diego, Calif.) with 0.15 mM calcium.

Transglutaminase (TG-1) Assay

Keratinocytes were placed in KGM (2 ml per well) at 0.2 million cells/plate in 6-well plates and grown for four or five days until the cells reached approximately 20% confluence. After removal of the old medium, 2 mL of fresh KGM were added to each well and 10 ul of corn oil containing 0, 2.5, or 5% cumic alcohol were placed on the surface of the medium each day for three days. One set of triplicate wells was left untreated to serve as control. After three days of incubation, cells were washed thoroughly with phosphate buffered saline (PBS, 10 mM sodium phosphate, 138 mM sodium choride, 2.7 mM potassium chloride, pH 7.4) and placed at −70 °C. for 2 hours. Cells were then thawed for two hours. The DNA content of cells was quantified by using the DNA-binding fluorophore, bis-benzimidazole (Hoechst 33258) and measuring the specific fluoroescence of the DNA-bound fluorophore (360 nm excitation, 450 nm emission). Cellular TG-1 levels were determined by using a transglutaminase-1 (TG-1) specific monoclonal antibody as the primary antibody (BC1, Amersham, UK) and a peroxidase labeled rabbit antimouse IgG as the secondary antibody (Amersham, UK). The plates were blocked at room temperature with 5% nonfat milk in Tris-buffered saline (TBS, 10 mM Tris, 150 mM NaCL, pH 8.0) for one hour followed by two hours incubation with the primary antibody (1:4000 dilution) in 1% milk/TBS at room temperature. After rinsing the plates three times with 1% milk/TDS containing 0.051% Tween 20 (Bio-Rad, Hercules, Calif.), the plates were incubated with a 1:4000 dilution of the secondary antibody at room temperature for two hours. The plates were then rinsed three times with 1% milk/0.05% Tween 20/TBS and three times with PBS. Color was developed by incubation with o-phenylene-diamine (Sigma, St. Louis. Mo.) and hydrogen peroxide (Sigma) dissolved in a 1:1 mixture of 0.2 M dibasic sodium phosphate (Sigma) and 0.1 M citric acid at pH 5.0(Sigma). Solutions were transferred to 4 ml plastic cuvets (Fisher Scientific, Pittsburgh Pa.) and the absorbance was read at 492 nm on an Ultraspec 3000 spectrophotometer (Pharmacia, Piscataway N.J.) and TG-1 levels were expressed as absorbence/DNA fluorescence.

Lipid Analysis

Keratinocytes were placed in KGM (2 ml per well) at 0.2 million per 6-well plates and grown for five days until approximately 20% confluence was reached. Cells were fed and treated with cumic alcohol as described above. After three days of treatment, cells were rinsed twice with PBS, then harvested by adding 3 ml of 0.1 N NaOH (Fisher) to each well and scraping with a rubber policeman. The supernatants were transferred to 16×100 mm glass test tubes with a teflon-coated caps and incubated for 1 hour at 70 °C. After cooling to room temperature a 50 $\mu$l aliquot was removed or protein determination (Pierce BCA assay, Rockford Ill.). To each tube 320 $\mu$l of 1 N HCI and 2.5 ml of chloroform were added and the tubes mixed well. The tubes were then placed on a tumbler and agitated for thirty minutes. The mixtures were then centrifuged for 10 minutes at 2000 ×g. Two milliliters of chloroform were removed from the organic phase and placed in an autosampler vial. The samples were then dried under $N_2$, resuspended in 60 $\mu$l of chloroform-:methanol 2:1 and transferred to an autosampler insert microtube which was placed inside another autosampler vial which was sealed. Forty $\mu$l of the sample was spotted (Camag Automatic TLC Sampler III, Wilmington, N.C.) on silica TLC plates (Whatman 4807-700) and the plates were developed in horizontal chambers (Camag) using the following solvent system: 1. 95:4.5:0.5 chloroform, methanol, acetic acid and 2. 60:40:2 hexane, ethyl ether, acetic acid. Following immersion In 10% copper sulfate in 8% phosphoric acid, plates were charred at 165 °C. for 20 minutes and then read in a densitometer (Camag TLC Scanner II).

Glucose Uptake Assay

Keratinocytes were plated in KGM medium at either 0.5 or 1 million cells/plate in six well plates and incuoated for 4 days. The medium was then aspirated, and the wells were rinsed twice with Phosphate Buffered Saline (PBS), then the plates were incubated (1 mL/well) for 24 hours. The medium was replaced with fresh KBM, 10 ul of corn oil containing cumic alcohol at various concentrations were added and cells were allowed to incubate (for 4 hours at 37C) before 2 $\mu$Ci of $^3$H 2-deoxy-glucose (Amersham, UK) were added to each well. Samples were then incubated for one hour. The medium was aspirated and wells were rinsed three times with PBS before the addition of 500 $\mu$L of 0.1N NaOH/well. After 10 minutes of agitation on a shaker, a 25 $\mu$L aliquot was removed for protein analysis, and 200 $\mu$L were transferred to a scintillation vial containing 5mL Scintillation cocktail (Scintiverse) and counting was performed on a Beckman counter, $^3$H-Glucose uptake results were expressed as CPM/$\mu$g protein.

Ascorbate Uptake Assay

For this experiment, third passage keratinocytes were plated into a KGM medium (Clonetics, Calif.) containing 0.15 mM calcium. About 80,000 cells were plated into each well of 6 well, cell-culture-treated plates and grown for 5 days, until the cells reached about 60–70% confluence.

Cells were then switched into fresh KBM and were treated with 5% cumic alcohol administered in corn oil (dosed 10 μl corn oil+active at indicated concentration/2 ml media). After 4 hours of incubation, 0.1 μCi/ml of L—$^{14}$C—1—ascorbic acid (Amersham, UK) and 50 units of ascorbic oxidase (Sigma) were added to each well and further incubated for 1 hour. The medium was aspirated and wells were rinsed 3 times with PBS before addition of 500 μl of 0.1N NaOH/well. After 10 minutes of agitation on shaker, 25 μL aliquot was removed for protein analysis, and 200 μl were transferred to scintillation vials containing 5 ml of scintiverse. The counting was performed on a Beckman counter (model LS 5801). Ascorbic acid uptake results were expressed as CPM /μg protein.

Concentrations used in the examples below are of cumic alcohol in a corn oil droplet. The in vitro concentration may not be relevant to in vivo concentration because there is partitioning between oil and culture medium and the medium concentration of the active is not The oil droplet concentration of the active. For the cumic alcohol to elicit its effect on the cultured cells, it must diffuse out of the corn oil into the culture medium where it is then accessible to the cells. The cumic alcohol concentration in the culture medium is therefore considerably less than the concentration in the corn oil droplet.

EXAMPLE 1

This example investigated the effect of cumic alcohol on glucose uptake in human keratinocytes. The results that were obtained are summarized in Table 1

TABLE 1

| SAMPLE | CPM/ug PROTEIN | % OF CONTROL | P VALUE | STATISTICAL SIGNIFICANCE |
|---|---|---|---|---|
| CONTROL | 19.77 +− 1.01 | 100 | — | — |
| CUMIC ALCOHOL 1% | 21.18 +− 0.84 | 107 | >0.05 | NO |
| CUMIC ALCOHOL 2.5% | 36.67 +− 1.04 | 185 | <0.05 | YES |
| CUMIC ALCOHOL 5% | 40.67 | 206 | <0.05 | YES |

It can be seen from the results in Table 1 that human keratinocytes treated with cumic alcohol showed substantially increased glucose uptake (with increases of 185 and 206% respectively) in comparison to untreated control cells.

EXAMPLE 2

This example investigated the effect of cumic alcohol on transglutaminase expression and ceramide production The results that were obtained are summarized in Tables 2 and 2A.

TABLE 2

| SAMPLE | TG-1 (abs/DNA) | % of CONTROL | P VALUE | STATISTICAL SIGNIFICANCE |
|---|---|---|---|---|
| Experiment 1 | | | | |
| CONTROL | 5.53 +− 0.67 | 100 | — | — |
| CUMIC ALCOHOL 2.5% | 6.48 +− 0.58 | 117 | >0.05 | NO |
| CUMIC ALCOHOL 5% | 9.94 +− 1.15 | 180 | <0.05 | YES |
| Experiment 2 | | | | |
| CONTROL | 6.41 +− 0.67 | 100 | — | — |
| CUMIC ALCOHOL 2.5% | 9.27 +− 0.40 | 145 | <0.05 | YES |

TABLE 2A

| SAMPLE | CERAMIDES (ng/ug PROTEIN) | % of CONTROL | P VALUE | STATISITICAL SIGNIFICANCE |
|---|---|---|---|---|
| Experiment 1 | | | | |
| CONTROL | 6.10 +− 2.01 | 100 | — | — |
| CUMIC ALCOHOL 2.5% | 4.03 +− 1.02 | 67 | >0.05 | NO |
| CUMIC ALCOHOL 5% | 9.37 +− 0.51 | 156 | <0.05 | YES |
| Experiment 2 | | | | |
| CONTROL | 1.76 +− 0.20 | 100 | — | — |
| CUMIC ALCOHOL 2.5% | 2.93 +− 0.12 | 166 | <0.05 | YES |
| CUMIC ALCOHOL 5% | 3.26 +− 0.41 | 185 | <0.05 | YES |

It can be seen from the results in Tables 2 and 2A that human keratinocytes treated with cumic alcohol at 2.5 and 5% showed increased expression of transglutaminase-1, a marker for differentiation and increased expression of ceramides, in comparison to untreated control cells.

EXAMPLE 3

This example investigated the effect of cumic alcohol on ascorbate uptake in human keratinocytes. The results that were obtained are summarized in Table 3.

TABLE 3

| SAMPLE | CPM/WELL | % of CONTROL | P VALUE | STATISTICAL SIGNIFICANCE |
|---|---|---|---|---|
| CONTROL | 13355 +− 938 | 100 | — | — |
| CUMIC ALCOHOL 5% | 17235 +− 398 | 129 | <0.05 | YES |

It can be seen from the results in Table 3 that human keratinocytes treated with cumic alcohol at 5% in corn oil significantly increased uptake of ascorbate in comparison to untreated control cells.

EXAMPLE 4

This example investigated the effect of cumic alcohol on transglutaminase and ceramide expression. The results that were obtained are summarized in Tables 4A and 4B.

TABLE 4A

| SAMPLE | TG-1 (ABS/DNA) | % of CONTROL | P VALUE | STATISTICAL SIGNIFICANCE |
|---|---|---|---|---|
| CONTROL | 12.73 +− 1.41 | 100 | — | — |
| CUMIC ALCOHOL 1% | 16.17 +− 5.37 | 127 | >0.05 | NO |
| CUMIC ALCOHOL 2.5% | 22.10 +− 1.74 | 174 | <0.05 | YES |
| CUMIC ALCOHOL 5% | 26.05 +− 2.73 | 205 | <0.05 | YES |

TABLE 4B

| SAMPLE | CERAMIDES (ng/ug PROTEIN) | % of CONTROL | P VALUE | STATISITICAL SIGNIFICANCE |
|---|---|---|---|---|
| Experiment 1 | | | | |
| CONTROL | 13.9 +− 3.6 | 100 | — | — |
| CUMIC ALCOHOL 1% | 12.5 +− 2.2 | 90 | >0.05 | NO |
| CUMIC ALCOHOL 2.5% | 19.4 +− 1.1 | 140 | >0.05 | NO |
| CUMIC ALCOHOL 5% | 41.5 +− | 299 | <0.05 | YES |

It can be seen from the results in Tables 4A and 4B that human keratinocytes treated with cumic alcohol showed significant increase in transglutaminase-1 expression and ceramide production. The inactivity at lower concentrations may be explained as stated in the paragraph immediately preceding the examples herein.

EXAMPLE 5

Example 5 illustrates topical compositions according to the present invention. The compositions can be processed in conventional manner. They are suitable for cosmetic use. In particular the compositions are suitable for application to wrinkled, rough, flaky, aged and/or UV-damaged skin and/or dry skin and post-menopausal skin to improve the appearance and the feel thereof as well as for application to healthy skin to prevent or retard deterioration thereof.

OIL-IN-WATER EMULSION

| INGREDIENT | % w/w |
|---|---|
| DI Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Cumic alcohol | 2.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total -> | 100.00 |
| DI Water | 71.20 |
| Xanthan Gum | 0.20 |
| Disodium EDTA | 0.10 |
| Glycerin | 5.00 |
| Butylene Glycol | 2.00 |
| Methylparaben | 0.30 |

-continued

OIL-IN-WATER EMULSION

| INGREDIENT | % w/w |
|---|---|
| Cumic alcohol | 2.00 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |

-continued

OIL-IN-WATER EMULSION

| INGREDIENT | % w/w |
|---|---|
| Propylparaben | 0.10 |
| Germall II | 0.10 |
| Fragrance | 0.10 |
| Total -> | 100.00 |

WATER-IN-OIL EMULSION

| INGREDIENT | % w/w |
|---|---|
| DI Water | 63.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| Cumic alcohol | 2.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Total -> | 100.00 |

HYDRO-GEL

| INGREDIENT | % w/w |
|---|---|
| DI Water | 81.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Cumic alcohol | 2.00 |
| Ascorbic acid | 1.00 |
| Methylparaben | 0.30 |
| Polysorbate 20 | 0.25 |
| Disodium EDTA | 0.10 |
| Germall II | 0.10 |
| Total -> | 100.00 |

ANHYDROUS SERUM

| INGREDIENT | % w/w |
|---|---|
| Cyclomethicone | 72.40 |
| Cumic alcohol | 1.00 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |

-continued

ANHYDROUS SERUM

| INGREDIENT | % w/w |
|---|---|
| Propylparaben | 0.20 |
| Fragrance | 0.10 |
| Total -> | 100.00 |

HYDRO-ALCOHOLIC GEL

| INGREDIENT | % w/w |
|---|---|
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Cumic alcohol | 1.00 |
| Methylparaben | 0.30 |
| Polysorbate 20 | 0.25 |
| Disodium EDTA | 0.10 |
| Germall II | 0.10 |
| Total -> | 100.00 |

It should be understood that the specific forms of the invention herein illustrated and described are intended to be representative only. Changes, including but not limited to those suggested in this specification may be made in the illustrated embodiments without departing from the clear teachings of the disclosure. Accordingly, reference should be made to the following appended claims in determining the full scope of the invention.

What is claimed is:

1. A cosmetic skin care composition comprising:
   (a) from 0.001 to 50 wt. % of solubilized, uncomplexed cumic alcohol of Formula I:

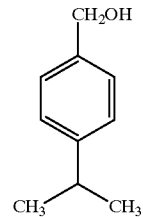

(b) a glucose compound, or a compound known to break down in the skin to glucose;
   (c) an ascorbate compound or a compound known to break down in the skin to ascorbic acid; and
   (d) a cosmetically acceptable vehicle.

2. The composition of claim 1 wherein said ascorbate compound is selected from the group consisting of ascorbic acid, ascorbyl palmitate, ascorbyl stearate, ascorbyl tetraisopalmitate, magnesium ascorbyl phosphate, sodium ascorbyl monophosphate, ascorbic acid polypeptide.

3. The composition according to claim 1 wherein said glucose compound is selected from the group consisting of glucose, glucosamine, glucose glutamate, galactose, lactose, sucrose and glucose phosphate esters.

4. The composition according to claim 1 wherein the composition is an oil-in-water emulsion and cumic alcohol is solubilized in the oil phase.

5. A cosmetic method of treating aged photoaged, dry, lined or wrinkled skin. the method comprising applying to the skin the composition according to claim 1.

6. A cosmetic method of improving the barrier function of the skin, the method comprising applying to the skin the composition according to claim 1.

7. A cosmetic method of improving keratinocyte differentiation, the method comprising applying to the skin the composition according to claim 1.

8. A cosmetic method of improving the lipid production by keratinocytes, the method comprising applying to the skin the composition according to claim 1.

9. A cosmetic method of improving the glucose uptake by keratinocytes, the method comprising applying to the skin the composition according to claim 1.

10. A cosmetic method of improving ascorbate uptake by keratinocytes, the method comprising applying to the skin the composition according to claim 1.

* * * * *